United States Patent [19]

Durlarch

[11] 4,215,136
[45] Jul. 29, 1980

[54] INSOLUBLE METAL SALTS OF N-ACETYL-TRYPTOPHANE AND USE THEREOF

[75] Inventor: Jean P. Durlarch, Paris, France

[73] Assignee: Cooperation Pharmaceutique Francaise, Melun, France

[21] Appl. No.: 799,532

[22] Filed: May 23, 1977

[30] Foreign Application Priority Data

May 26, 1976 [FR] France .................................. 76 16121

[51] Int. Cl.² .................... A61K 31/405; C07D 209/20
[52] U.S. Cl. ............................ 424/274; 260/326.14 T
[58] Field of Search ................ 260/326.14 T; 424/274

[56] References Cited

U.S. PATENT DOCUMENTS 3,345,264  10/1967  Bocher .................................. 424/274

FOREIGN PATENT DOCUMENTS 557705  5/1958  Canada ............................. 260/326.14 T
40-23659 10/1965 Japan ............................. 260/326.14 R

*Primary Examiner*—Donald G. Daus
*Assistant Examiner*—D. B. Springer
*Attorney, Agent, or Firm*—Larson, Taylor and Hinds

[57] ABSTRACT

The invention concerns: novel insoluble derivatives of N-acetyl-tryptophane characterized by the following general formula:

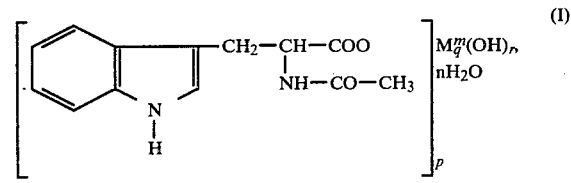

in which:
M represents an atom of aluminium, of titanium or of bismuth of valency m,
p and q are whole numbers, at least equal to 1,
r is a whole number at least equal to 1 or 0, with $m \times q = p + r$,
n is 0 or a whole or fractional number their preparation and medicaments containing them.

6 Claims, No Drawings

INSOLUBLE METAL SALTS OF N-ACETYL-TRYPTOPHANE AND USE THEREOF

The invention relates to novel insoluble derivatives of N-acetyl-tryptophane as well as to their use as topical medicaments, notably as gastrointestinal dressings.

There are already known soluble salts of N-acetyl-tryptophane obtained from alkali or alkaline-earth metals. These salts, described in patent application No. Fr 74 42505 of Dec. 23, 1974, have neurotropic properties, issued July 23, 1976, Ser. No. 2,295,746.

The novel derivatives according to the invention correspond to the general formula I

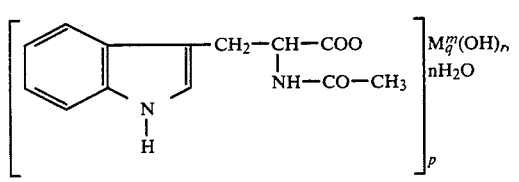

in which:
M represents an aluminium, titanium or bismuth atom of valency m,
p and q are whole numbers at least equal to 1,
r is a whole number at least equal to 1 or 0, with $m \times q = p + r$,
n is 0 or a whole or fractional number.

It has been found unexpectedly that these derivatives have valuable anti-ulcer properties and notably an interesting gastrointestinal topical action.

Acetyl-tryptophane, in the above-said general formula I, may be in the D, DL or L form.

Exceptionally interesting results have been obtained with derivatives of formula I in which M represents aluminium.

To prepare the compounds according to the invention, it is possible to resort to the reaction, in a basic medium, notably at pH 9, of D, DL or L N-acetyl-tryptophane with a salt of the selected metal; the salt used can be notably the chloride or the sulphate; it may be used to slight excess.

The reaction is effected with stirring and, preferably, with heating of the reaction mixture.

The desired compound precipitates in part when hot. After cooling it is separated by draining and rinsing with water until neutrality.

In this way the two compounds in which M is respectively aluminium and titanium were prepared.

EXAMPLE 1

Preparation of monobasic-(DL) aluminium N-acetyl-tryptophanate (referred to below as compound A)

The formula of this derivative is:

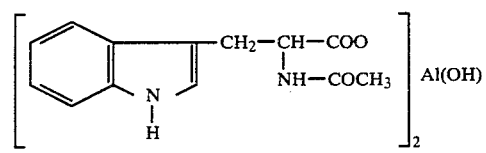

In a round bottom flask of 1 liter, are mixed at ambient temperature, 550 g of water, 15 g of soda in pellets and 61.5 g of (DL) N-acetyl-tryptophane. In this manner a limpid solution is obtained.

To this solution 36 g of $AlCl_3, 6H_2O$ dissolved in 100 ml of water is added. The mixture is heated for one hour at 60° C. and the temperature is allowed to return to 20° C. The aluminium derivative which is formed is drained, washed with water then with hexane and dried at 100° C. in a ventilated oven.

54 g obtained (yield 80%) of a clear beige powder, whose melting point is higher than 300° C. (KOFLER bench).

Elemental analysis of the dried product:

|  | C | H | N | Al |
|---|---|---|---|---|
| Calculated: | 58.4 | 5.06 | 5.24 | 5.05 |
| Found: | 58.9 | 5.21 | 5.21 | 5.15 |

EXAMPLE 2

Preparation of (DL) titanium N-acetyl-tryptophanate (here below referred to as compound B)

The probable formula of this derivative is:

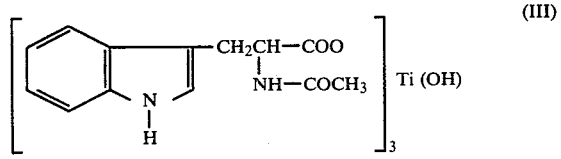

18.45 g of (DL) N-acetyl-tryptophane and 3 g of soda are dissolved in 100 g of water.

To this solution a mixture of 7.35 g of titanium sulphate, and 50 g of water is added. The whole is brought to reflux (80°–90° C.) for 1 hour with stirring. It is re-cooled and the desired compound is separated by draining.

It is washed with water until neutrality and dried in the oven until the weight is constant.

19 g (Yield: 80%) are obtained of a beige powder whose melting point is higher than 300° C. (KOFLER bench).

The elementary analysis of this compound in the dried state gives results which enable, to a good approximation, the conclusion to be drawn that it is indeed a compound of Formula III. In fact, it has been found (the "calculated" values corresponding to Formula III):

|  | C | H | N | Ti |
|---|---|---|---|---|
| Calculated: | 59.2 | 5.06 | 10.63 | 6.07 |
| Found: | 55.9 | 5.10 | 9.81 | 6.40 |

It is also possible to provide for the preparation of other compounds in which p, q and r would have other values, by causing the proportions and constituents of the reaction to vary as well as the conditions of the latter.

The compounds according to the invention were subjected to the pharmacological tests described below.

I Antiulcer activity:

(A) Tests by the technique called "Shay ulcer" [Gastroenterology, 5, 43, (1945)].

The study was carried out on female rats [Sprague-Dawley OFA Iffa-Credo] weighing 170±10 g, conforming to the experimental protocol described below.

After fasting 48 hours, during which the rats had always available to them a 20% glucose solution, the pylorus was ligated and all beverage was eliminated.

Compound A in the form of two suspensions respectively 5 and 10% in distilled water containing 3% of gum arabic was administered orally and before the ligature of the pylorus to three groups of animals, the animals of the first two groups receiving the 5% solution and those of the third the 10% solution. These three groups of animals received active substance to the extent respectively of 250 mg/kg as regards those of the first group, 500 mg/kg as regards those of the second and 1000 mg/kg those of the third. A fourth group and control group of animals received 10 ml/kg of bidistilled water.

In the case of compound B, the procedure was similar using similar suspensions, the doses administered being respectively 750, 1000 and 1500 mg/kg.

After a period of 18 hours, the animals were sacrificed and the stomachs removed.

The tests having been carried out with aluminium acetyl-tryptophanate (compound A), on the one hand, and with titanium acetyl-tryptophanate (compound B), on the other hand, for each of these compounds there was determined, the "anti-ulcer dose 50" (or again active dose AD 50) by oral administration; for this determination the method of Litchfield and Wilcoxon [J. Pharmacol. 96, 98–111 (1949)], was employed. The results obtained are as follows:

| Derivative | AD 50 (mg/kg) |
|---|---|
| Aluminium N-acetyltryptophanate | 550 |
| Titanium N-acetyltryptophanate | 1178 |

Since it could be considered that the activity of the derivatives according to the invention were attributable to the presence of $Al^{3+}$ or $Ti^{4+}$ ions in these derivatives, comparative tests were carried out with compounds including respectively each of these ions, namely Kaolin $Al_4[Si_4O_{10}]$ $(OH)_8$ and titanium oxide $TiO_2$.

The AD 50 of compound A (of aluminium N-acetyltryptophanate) being 550 mg/kg, it should correspond, for an equal dose of aluminium, to an AD 50 of 130 mg/kg for Kaolin if the activity of the compound A was due solely to the presence of the $AL^{3+}$ ion. In fact, the AD 50 of kaolin is much higher; it is 925 mg/kg, that is to say about 7 times higher than that which could be expected.

By reasoning and proceeding similarly for titanium, similar results were obtained using titanium oxide (AD 50 of 700 mg/kg by the buccal route) showing that the latter is about 7 times less active than compound B (titanium N-acetyl-tryptophanate) if reference is made to the amounts of titanium employed.

In conclusion, the activity in these tests, of derivatives A and B according to the invention is about 7 times higher than the activity which could be expected by reason of the presence of the $Al^{3+}$ and the $Ti^{4+}$ ions alone.

(B) Tests according to the technique called "stress ulcer". Rossi and Bonfils—Compte rendus de la Societe de Biologie, (1956), 150, page 2124.

The study was carried out on female S.P.F. Sprague-Dawley OFA Iffa-Credo rats, weighing 140±10 g and adhering to the following experimental protocol.

To cause the ulcer, the animals were immobilized in a flexible grid with meshes of 4×4 mm and suspended horizontally; they received neither food nor drink. They were sacrificed at the end of 24 hours. The stomachs were removed and opened and then the ulcers were counted with a binocular lens.

Each stomach was assessed according to the method of J. M. LWOFF and the ulceration index calculated.

The compound A suspended in distilled water with 3% of gum arabic was administered 48 hours and 24 hours before and at the time of placing under stress to three groups of animals. These animals each received by the oral route, 500, 1000 and 1500 mg/kg of this compound according to their group.

A control group received for three days, orally gummy water in the amount of 1 ml/100 g.

The AD 50 of compound A found according to this technique was equal to 700 mg/kg by the buccal route.

As in the case of "Shay ulcer" the same study was reproduced with kaolin.

The kaolin was suspended in distilled water with 3% of gum arabic and was administered by the buccal route 48 hours and 24 hours before and at the time of placing under stress.

Three groups of animals received respectively 1000, 2000 and 3000 mg/kg of kaolin by the buccal route.

Proceeding as in the case of compound A, it was possible to determine the $AD_{50}$ of kaolin which is 2700 mg/kg, whilst, if the activity of compound A was due to the presence alone of the aluminium, to an $AD_{50}$ of 700 mg/kg for A there should correspond an $AD_{50}$ of 165 mg/kg for the kaolin.

The results obtained showed that the superiority of compound A is still much more marked with regard to the "stress ulcer" than with regard to "Shay ulcer".

(C) Tests according to the "stress ulcer" technique aggravated by para-chloro-phenyl-alanine (PCPA) administered in a non-blocking dose.

The rats used were of the same sex, same strain and had the same weight as those used in the tests described under B. The experimental protocol was also the same.

However, in these tests the rats received intraperitoneally, at the time of stressing, 100 mg/kg of PCPA in suspension in distilled water including 3% of gum arabic and an "absolute control" group was provided having received no preparation before placing under stress.

By reason of the aggravation of the ulcers caused by the PCPA, the Lwoff assessment is no longer usable and is replaced by the following:

0 : no ulcer
1 : one to two ulcers
2 : three to four ulcers } in the form of more or less hollow "pits"
3 : five ulcers
4 : six to ten ulcers
5 : one to two ulcers } in the form of "furrows" measuring at least 5 mm in length
6 : three to four ulcers
with a maximum of 4 + 6 = 10.

In this way it was possible to determine the ulceration index and the percentage inhibition with respect to the controls.

The results obtained enabled it to be shown that, according to this technique, the anti-ulcer activity of compound A is still considerable ($AD_{50}$=1325 mg/kg by the oral route) taking into account the considerable aggravation of the ulcers due to the PCPA.

In the course of these same tests kaolin was shown to be inactive.

(D) Study of the anti-ulcer activity of compound A (D,L) and of compound B (D,L) after administering reserpine.

The technique used was that of Cohen and A. Pessonnier (Ann. Pharm. Fr (1963) 21, 215-22) according to the following protocol:

Sprague-Dawley female rats were used, of OFA S.P.F. Iffa Credo strain weighing 150±20 g;

the rats received a single injection by the intraperitoneal route of 5 mg/kg of reserpine in solution in 0.25% acetic acid;

the compound studied were administered twice by the buccal route: three hours before and three hours after the injection of reserpine;

the rats were sacrificed 20 hours after the injection of reserpine;

the assessment was established as follows:

```
0 = no ulcer
1 = one to two ulcers    ⎞  in the form of small
                         ⎟  "erosions"
2 = more than two ulcers ⎠
3 = one to two ulcers    ⎞  in the form of more or
                         ⎟  less deep "pits"
4 = more than two ulcers ⎠
5 = one to two ulcers    ⎞  in the form of "furrows"
                         ⎟  measuring at least 5 mm
6 = more than two ulcers ⎠  in length
Maximum assessment for one stomach : 2 + 4 + 6 = 12
```

From the results obtained the ulceration index was deduced; the percentage of inhibition was calculated with respect to the index obtained in the controls.

The values of the $AD_{50}$ calculated according to the method of Litchfield and Wilcoxon are:

Compound A: $AD_{50} = 1447$ mg/kg (p.o.)
Compound B: $AD_{50} = 1550$ mg/kg (p.o.)
Kaolin and titanium oxide are inactive in this test.

II—Activity on intestinal passage:

Protocol:

Male mice, fasting for 24 hours, weighing 18-20 g. were used.

The substances to be tested were administered buccally before a suspension of vegetable carbon (10 g/100 ml).

After 10 minutes, the animals were bled and the intestine was removed and examined.

No significant increase, with respect to the controls, of the intestinal passage was noted for doses of 2, 4 and 6 g/kg of compound A and 2 g/kg of compound B.

III—Action on the central nervous system:

(A) Interaction with a monoamine-oxidase inhibitor (MAOI):

Sprague-Dawley male rats of OFA strain received 20 mg/kg intra peritoneally of Tylciprine (MAOI) and twenty minutes later, 3 g/kg of compound A (D,L) bucally.

Hyperthermia was observed which commenced fairly rapidly with a maximum after 185 minutes and a hyperactivity after 80 minutes with a maximum at 155 minutes.

The hyperthermia and the hyperactivity observed indicate an apparently central nervous serotoninergic action, that is to say antidepressive, of compound A (comparable activities are obtained with L-tryptophane).

If the dose of compound A (D,L) is only 2 g/kg, it does not cause hyperthermia but only a notable hyperactivity.

(B) Interaction with a MAOI after treatment with P.C.P.A.

If the test is renewed under the same conditions but on male rats previously treated by decreasing doses of P.C.P.A. which is a tryptophane-hydroxylase inhibitor, it is observed that:

after treatment for 2 days by 50 mg/kg PCPA, the compound A causes neither hyperthermia nor hyperactivity, after treatment for 1 day by 12.5 mg/kg of PCPA, compound A causes the appearance of the first signs of hyperactivity and after treatment for 1 day by 6 mg/kg of PCPA, compound A causes a notable hyperactivity, without variation in the rectal temperature.

This test shows that the central activity of compound A is in fact serotoninergic since PCPA prevents the appearance of the hyperactivity-hyperthermia syndrome provoked by the association tylciprine—compound A. In conclusion:

The preceding tests showed that compound A possesses, besides local topical properties, a neurotropic property of serotoninergic type connected with the passage of its anion through the hemato-cerebral barrier.

IV—Determination of the toxicity:

By oral administration of the derivatives according to the invention, no mortality was observed after six days for total doses of 15 g/kg for compound A and 10 g/kg for compound B.

It follows that the "lethal dose 50" or $LD_{50}$ is higher than these values. No more precise determination was made, considering these values are already very high.

Knowing that the inocuousness of a medicament is all the greater as the ratio AD 50/LD is smaller, it can be said that the derivatives according to the invention with values respectively of this ratio less than 0.03 (compound A) and 0.12 (compound B) are very "safe".

These different results are assembled in the following table:

| Compound | AD 50 mg/kg (orally) | LD 50 mg/kg (orally) | AD 50/LD 50 |
|---|---|---|---|
| A | 550 | > 15000 | < 0.03 |
| B | 1178 | > 10000 | < 0.12 |

The derivatives according to the invention are particularly effective as topical digestive remedies. For this use, their insolubility confers on them a maximum activity for a minimum toxicity.

These derivatives are also active as topical cutaneous remedies in cosmetology and in dermatology.

For their use in therapeutics, the derivatives according to the invention may be offered in forms administered orally such as tablets, suspensions, granules, powders and sachets.

These derivatives can also form part of the composition of suppositories.

For cutaneous applications in cosmetology and dermatology, these derivatives can be used notably in the form of ointments and creams.

For oral applications, there are used preferentially in the adult, doses of 1 to 10 g of active principle per day.

When the pharmaceutical form used is constituted by sachets, the latter can contain from 3 to 5 g of active principle; in the case of tablets the content of active substance is from 0.5 to 1 g.

For the preparation of sweetened or unsweetened granules, it is possible to use as the active principle, one or several derivatives according to the invention, alone or associated with anti-spasmodic and/or antiseptic agents.

In all cases of types administered orally, the active substance which comprises one or several derivatives according to the invention is associated with adjuvants and/or excipients customarily used in galenical practice.

For administration rectally, the active substance which comprises one or several of the derivatives according to the invention is associated with an excipient with a low melting point provided for this purpose.

EXAMPLE.

By a customary method there are prepared tablets containing 600 mg of active principles and having the following composition

| | |
|---|---|
| Aluminium N-acetyl-tryptophane derivative according to example 1 | 600 mg |
| Starch | 160 mg |
| Precipitated silica | 100 mg |
| Magnesium stearate | 5 mg. |

As is self-evident and as emerges already from the foregoing, the invention is in no way limited to those embodiments and types of application which have been more especially considered; it encompasses, on the contrary, all modifications.

I claim:

1. A compound of the formula:

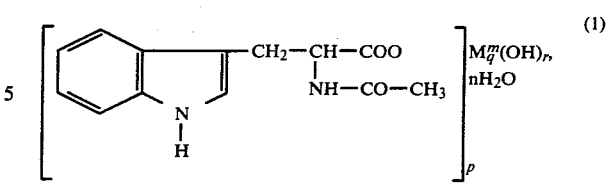

in which:
M represents an atom of aluminium, of titanium or of bismuth of valency m,
p and q are whole numbers at least equal to 1,
r is 0 or a whole number at least equal to 1, with $m \times qq = p + r$,
n is 0 or a whole or fractional number.

2. (DL)—monobasic aluminium N-acetyl-tryptophanate of the formula

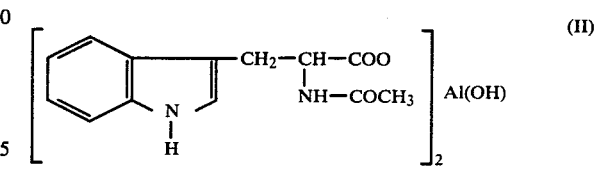

3. (DL) monobasic titanium N-acetyl-tryptophanate of the formula:

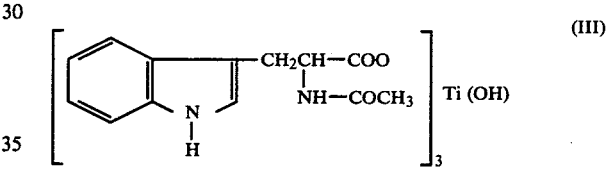

4. (DL)—monobasic aluminium N-acetyl-tryptophanate characterized by the fact that it has been obtained by reaction of 61.5 g of (DL) N-acetyl-tryptophane and 36 g of aluminum chloride hexahydrate in the presence of 15 g of soda in pellets dissolved in 550 g of water at 60° C.

5. (DL) monobasic titanium N-acetyl-tryptophanate, characterized by the fact that it has been obtained by the reaction of 18.45 g of (DL) N-acetyl-tryptophane and 7.35 g of titanium sulphate in the presence of 3 g of soda dissolved in 100 g of water at reflux temperature.

6. A medicament useful as an anti-ulcer agent characterized by the fact it comprises as an active substance, an effective amount of at at least one compound according to claim 1 and a material selected from the group consisting of adjuvants and excipients.

* * * * *